(12) United States Patent
Madison et al.

(10) Patent No.: US 6,797,504 B1
(45) Date of Patent: Sep. 28, 2004

(54) INHIBITORS OF SERINE PROTEASE ACTIVITY OF MATRIPTASE OR MTSP1

(75) Inventors: Edwin L. Madison, San Diego, CA (US); Joseph Edward Semple, San Diego, CA (US); Gary Samuel Coombs, San Diego, CA (US); John Eugene Reiner, San Diego, CA (US); Edgar O. Ong, San Diego, CA (US); Gian Luca Araldi, Quincy, MA (US)

(73) Assignee: Dendreon San Diego LLC, Seattle, WA (US)

( * ) Notice: Subject to any disclaimer, the term of this patent is extended or adjusted under 35 U.S.C. 154(b) by 188 days.

(21) Appl. No.: 09/657,986

(22) Filed: Sep. 8, 2000

(51) Int. Cl.[7] .......................... C12N 9/64; C12N 15/09; A01N 43/00; A01N 43/54; A01N 43/40; A01N 43/64; A01N 43/36; A01N 37/00; A01N 37/12; A01N 37/30; A01N 41/06

(52) U.S. Cl. ................. 435/226; 435/69.2; 514/211.05; 514/274; 514/326; 514/336; 514/381; 514/428; 514/512; 514/513; 514/564; 514/601

(58) Field of Search ................................ 435/219, 69.2, 435/226; 562/440, 442, 430, 439; 514/564, 211.05, 326, 336, 381, 428, 512, 513, 601; 560/29, 35, 19, 34, 80; 540/523; 546/17, 213; 548/280.4, 537, 253; 558/260, 276; 564/80

(56) References Cited

U.S. PATENT DOCUMENTS

| | | | | |
|---|---|---|---|---|
| 5,492,895 A | * | 2/1996 | Vlasuk et al. | ................. 514/18 |
| 5,696,231 A | * | 12/1997 | Abelman et al. | ........... 530/331 |
| 5,776,927 A | * | 7/1998 | Abelman et al. | ........... 514/210 |
| 5,955,576 A | * | 9/1999 | Vlasuk et al. | .............. 530/331 |
| 6,294,663 B1 | * | 9/2001 | O'Brien et al. | ............ 536/23.5 |

FOREIGN PATENT DOCUMENTS

| | | |
|---|---|---|
| WO | WO 95/28420 | 10/1995 |
| WO | WO 96/19493 | 6/1996 |
| WO | WO 96/40743 | 12/1996 |
| WO | WO 00/05245 | 2/2000 |
| WO | WO 00/53232 A1 * | 9/2000 |
| WO | WO 01/97794 A2 * | 12/2001 |
| WO | WO 02/20475 A2 * | 4/2002 |

OTHER PUBLICATIONS

Lin C.–Y et al. Molecular cloning of cDNA for matriptase, a matrix–degrading serine protease with trypsin–like activity. J. Biol. Chem. (1999) 274, 18231–18236.*

Lin C.–Y. et al. Purification and charcterization of a complex containing matriptease and a Kunitz–type serine protease inhibitor from human milk. J. Biol. Chem. (1999), 274, 18237–18242.*

Enyedy I. et al. Structure–based approach for the discovery of bis–benzamidines as novel inhibitors of matriptase, J. Med. Chem. (2001) 44, 1349–1355.*

Long Y.–Q. et al. Synthesis and evaluation of the sunflower derived trypsin inhibitor as a potent inhibitor of the type II transmembrane serine protease, matriptase, Bioorganic and Medicinal Chemistry Letters, (2001) 11, 2515–2519.*

* cited by examiner

Primary Examiner—Rebecca E. Prouty
Assistant Examiner—Malgorzata A. Walicka
(74) Attorney, Agent, or Firm—Townsend and Townsend and Crew LLP

(57) ABSTRACT

The present invention provides compounds which inhibit serine protease activity of matriptase or MTSP1. Also provided are pharmaceutical compositions comprising those compounds and methods of using the compounds and pharmaceutical compositions to treat conditions ameliorated by inhibition of matriptase or MTSP1. The invention provides recombinant serine protease domains and methods of using peptides comprising a recombinant serine protease domain to screen for compounds that inhibit serine protease activity of matriptase or MTSP1.

4 Claims, 8 Drawing Sheets

Figure 1A

| Compd # | MOLSTRUCTURE |
|---------|--------------|
| 1 | |
| 2 | |
| 3 | |
| 4 | |
| 5 | |
| 6 | |
| 7 | |

Figure 1B

| Compd # | MOLSTRUCTURE |
|---|---|
| 8 | |
| 9 | |
| 10 | |
| 11 | |
| 12 | |
| 13 | |
| 14 | |

```
         10        20        30        40        50        60
GTTGTTGGGGGCACGGATGCGGATGAGGGCGAGTGGCCCTGGCAGGTAAGCCTGCATGCT
CAACAACCCCCGTGCCTACGCCTACTCCCGCTCACCGGGACCGTCCATTCGGACGTACGA
 V  V  G  G  T  D  A  D  E  G  E  W  P  W  Q  V  S  L  H  A>

70        80        90       100       110       120
CTGGGCCAGGGCCACATCTGCGGTGCTTCCCTCATCTCTCCCAACTGGCTGGTCTCTGCC
GACCCGGTCCCGGTGTAGACGCCACGAAGGGAGTAGAGAGGGTTGACCGACCAGAGACGG
 L  G  Q  G  H  I  C  G  A  S  L  I  S  P  N  W  L  V  S  A>

130       140       150       160       170       180
GCACACTGCTACATCGATGACAGAGGATTCAGGTACTCAGACCCCACGCAGTGGACGGCC
CGTGTGACGATGTAGCTACTGTCTCCTAAGTCCATGAGTCTGGGGTGCGTCACCTGCCGG
 A  H  C  Y  I  D  D  R  G  F  R  Y  S  D  P  T  Q  W  T  A>

190       200       210       220       230       240
TTCCTGGGCTTGCACGACCAGAGCCAGCGCAGCGCCCCTGGGGTGCAGGAGCGCAGGCTC
AAGGACCCGAACGTGCTGGTCTCGGTCGCGTCGCGGGGACCCCACGTCCTCGCGTCCGAG
 F  L  G  L  H  D  Q  S  Q  R  S  A  P  G  V  Q  E  R  R  L>

250       260       270       280       290       300
AAGCGCATCATCTCCCACCCCTTCTTCAATGACTTCACCTTCGACTATGACATCGCGCTG
TTCGCGTAGTAGAGGGTGGGGAAGAAGTTACTGAAGTGGAAGCTGATACTGTAGCGCGAC
 K  R  I  I  S  H  P  F  F  N  D  F  T  F  D  Y  D  I  A  L>

310       320       330       340       350       360
CTGGAGCTGGAGAAACCGGCAGAGTACAGCTCCATGGTGCGGCCCATCTGCCTGCCGGAC
GACCTCGACCTCTTTGGCCGTCTCATGTCGAGGTACCACGCCGGGTAGACGGACGGCCTG
 L  E  L  E  K  P  A  E  Y  S  S  M  V  R  P  I  C  L  P  D>
```

FIGURE 3B

```
        370       380       390       400       410       420
GCCTCCCATGTCTTCCCTGCCGGCAAGGCCATCTGGGTCACGGGCTGGGGACACACCCAG
CGGAGGGTACAGAAGGGACGGCCGTTCCGGTAGACCCAGTGCCCGACCCCTGTGTGGGTC
 A  S  H  V  F  P  A  G  K  A  I  W  V  T  G  W  G  H  T  Q>

430       440       450       460       470       480
TATGGAGGCACTGGCGCGCTGATCCTGCAAAAGGGTGAGATCCGCGTCATCAACCAGACC
ATACCTCCGTGACCGCGCGACTAGGACGTTTTCCCACTCTAGGCGCAGTAGTTGGTCTGG
 Y  G  G  T  G  A  L  I  L  Q  K  G  E  I  R  V  I  N  Q  T>

490       500       510       520       530       540
ACCTGCGAGAACCTCCTGCCGCAGCAGATCACGCCGCGCATGATGTGCGTGGGCTTCCTC
TGGACGCTCTTGGAGGACGGCGTCGTCTAGTGCGGCGCGTACTACACGCACCCGAAGGAG
 T  C  E  N  L  L  P  Q  Q  I  T  P  R  M  M  C  V  G  F  L>

550       560       570       580       590       600
AGCGGCGGCGTGGACTCCTGCCAGGGTGATTCCGGGGGACCCCTGTCCAGCGTGGAGGCG
TCGCCGCCGCACCTGAGGACGGTCCCACTAAGGCCCCCTGGGGACAGGTCGCACCTCCGC
 S  G  G  V  D  S  C  Q  G  D  S  G  G  P  L  S  S  V  E  A>

610       620       630       640       650       660
GATGGGCGGATCTTCCAGGCCGGTGTGGTGAGCTGGGGAGACGGCTGCGCTCAGAGGAAC
CTACCCGCCTAGAAGGTCCGGCCACACCACTCGACCCCTCTGCCGACGCGAGTCTCCTTG
 D  G  R  I  F  Q  A  G  V  V  S  W  G  D  G  C  A  Q  R  N>

670       680       690       700       710       720
AAGCCAGGCGTGTACACAAGGCTCCCTCTGTTTCGGGACTGGATCAAAGAGAACACTGGG
TTCGGTCCGCACATGTGTTCCGAGGGAGACAAAGCCCTGACCTAGTTTCTCTTGTGACCC
 K  P  G  V  Y  T  R  L  P  L  F  R  D  W  I  K  E  N  T  G>
```

GTATAG

CATATC

SEQUENCE LISTING

```
<160> NUMBER OF SEQ ID NOS: 11

<210> SEQ ID NO 1
<211> LENGTH: 726
<212> TYPE: DNA
<213> ORGANISM: Homo Sapiens
<220> FEATURE:
<221> NAME/KEY: misc_feature
<223> OTHER INFORMATION: Nucleic acid sequence of protease domain of
      MTSP1

<400> SEQUENCE: 1
gttgttgggg gcacggatgc ggatgagggc gagtggccct ggcaggtaag cctgcatgct      60
ctgggccagg gccacatctg cggtgcttcc ctcatctctc ccaactggct ggtctctgcc     120
gcacactgct acatcgatga cagaggattc aggtactcag accccacgca gtggacggcc     180
ttcctgggct tgcacgacca gagccagcgc agcgccctg gggtgcagga gcgcaggctc      240
aagcgcatca tctcccaccc cttcttcaat gacttcacct tcgactatga catcgcgctg     300
ctggagctgg agaaaccggc agagtacagc tccatggtgc ggcccatctg cctgccggac     360
gcctcccatg tcttccctgc cggcaaggcc atctgggtca cgggctgggg acacacccag     420
tatggaggca ctggcgcgct gatcctgcaa aagggtgaga tccgcgtcat caaccagacc     480
acctgcgaga acctcctgcc gcagcagatc acgccgcgca tgatgtgcgt gggcttcctc     540
agcggcggcg tggactcctg ccaggtgat tccgggggac ccctgtccag cgtggaggcg      600 gatggcgga tcttccaggc cggtgtggtg agctggggag acggctgcgc tcagaggaac      660
aagccaggcg tgtacacaag gctccctctg tttcgggact ggatcaaaga gaacactggg     720
gtatag                                                               726

<210> SEQ ID NO 2
<211> LENGTH: 241
<212> TYPE: PRT
<213> ORGANISM: Homo Sapiens
```

```
<400> SEQUENCE: 2

Val Val Gly Gly Thr Asp Ala Asp Glu Gly Glu Trp Pro Trp Gln Val
1               5                   10                  15

Ser Leu His Ala Leu Gly Gln Gly His Ile Cys Gly Ala Ser Leu Ile
            20                  25                  30

Ser Pro Asn Trp Leu Val Ser Ala Ala His Cys Tyr Ile Asp Asp Arg
            35                  40                  45

Gly Phe Arg Tyr Ser Asp Pro Thr Gln Trp Thr Ala Phe Leu Gly Leu
        50                  55                  60

His Asp Gln Ser Gln Arg Ser Ala Pro Gly Val Gln Glu Arg Arg Leu
65                  70                  75                  80

Lys Arg Ile Ile Ser His Pro Phe Phe Asn Asp Phe Thr Phe Asp Tyr
                85                  90                  95

Asp Ile Ala Leu Leu Glu Leu Glu Lys Pro Ala Glu Tyr Ser Ser Met
            100                 105                 110

Val Arg Pro Ile Cys Leu Pro Asp Ala Ser His Val Phe Pro Ala Gly
            115                 120                 125

Lys Ala Ile Trp Val Thr Gly Trp Gly His Thr Gln Tyr Gly Gly Thr
130                 135                 140

Gly Ala Leu Ile Leu Gln Lys Gly Glu Ile Arg Val Ile Asn Gln Thr
145                 150                 155                 160

Thr Cys Glu Asn Leu Leu Pro Gln Gln Ile Thr Pro Arg Met Met Cys
                165                 170                 175

Val Gly Phe Leu Ser Gly Gly Val Asp Ser Cys Gln Gly Asp Ser Gly
            180                 185                 190

Gly Pro Leu Ser Ser Val Glu Ala Asp Gly Arg Ile Phe Gln Ala Gly
            195                 200                 205

Val Val Ser Trp Gly Asp Gly Cys Ala Gln Arg Asn Lys Pro Gly Val
            210                 215                 220

Tyr Thr Arg Leu Pro Leu Phe Arg Asp Trp Ile Lys Glu Asn Thr Gly
225                 230                 235                 240

Val

<210> SEQ ID NO 3
<211> LENGTH: 23
<212> TYPE: DNA
<213> ORGANISM: Artificial Sequence
<220> FEATURE:
<223> OTHER INFORMATION: Description of artificial sequence: PC-3 sscDNA
      sense oligonucleoide primer
<220> FEATURE:
<221> NAME/KEY: misc_feature
<222> LOCATION: (0)...(0)
<223> OTHER INFORMATION: N=Inosine

<400> SEQUENCE: 3
tggrtnvtnw sngcnrcnca ytg                                        23

<210> SEQ ID NO 4
<211> LENGTH: 30
<212> TYPE: DNA
<213> ORGANISM: Artificial Sequence
<220> FEATURE:
<223> OTHER INFORMATION: Description of artificial sequence: PC-3 sscDNA
      anti-sense oligonucleoide primer
<220> FEATURE:
<221> NAME/KEY: misc_feature
<222> LOCATION: (0)...(0)
<223> OTHER INFORMATION: N=Inosine
```

```
<400> SEQUENCE: 4
nggnccnccn swrtcnccyt nrcanghrtc                              30

<210> SEQ ID NO 5
<211> LENGTH: 28
<212> TYPE: DNA
<213> ORGANISM: Artificial Sequence
<220> FEATURE:
<223> OTHER INFORMATION: Description of artificial sequence:
      oligonucleoide primer

<400> SEQUENCE: 5
caccccttct tcaatgactt caccttcg                                28

<210> SEQ ID NO 6
<211> LENGTH: 18
<212> TYPE: DNA
<213> ORGANISM: Artificial Sequence
<220> FEATURE:
<223> OTHER INFORMATION: Description of artificial sequence:
      oligonucleoide primer

<400> SEQUENCE: 6
tacctctcct acgactcc                                           18

<210> SEQ ID NO 7
<211> LENGTH: 25
<212> TYPE: DNA
<213> ORGANISM: Artificial Sequence
<220> FEATURE:
<223> OTHER INFORMATION: Description of artificial sequence:
      oligonucleoide primer

<400> SEQUENCE: 7
gaggttctcg caggtggtct ggttg                                   25

<210> SEQ ID NO 8
<211> LENGTH: 39
<212> TYPE: DNA
<213> ORGANISM: Artificial Sequence
<220> FEATURE:
<223> OTHER INFORMATION: Description of artificial sequence:
      oligonucleoide primer

<400> SEQUENCE: 8
ctcgagaaaa gagttgttgg gggcacggat gcggatgag                    39

<210> SEQ ID NO 9
<211> LENGTH: 36
<212> TYPE: DNA
<213> ORGANISM: Artificial Sequence
<220> FEATURE:
<223> OTHER INFORMATION: Description of artificial sequence:
      oligonucleoide primer

<400> SEQUENCE: 9
gcggccgcac tatacccag tgttctcttt gatcca                        36

<210> SEQ ID NO 10
<211> LENGTH: 9
<212> TYPE: PRT
<213> ORGANISM: Homo Sapiens

<400> SEQUENCE: 10

Val Val Gly Gly Thr Asp Ala Asp Glu
```

-continued

```
<210> SEQ ID NO 11
<211> LENGTH: 726
<212> TYPE: DNA
<213> ORGANISM: Homo Sapiens
<220> FEATURE:
<221> NAME/KEY: misc_feature
<223> OTHER INFORMATION: Nucleic acid sequence of protease domain of
      MTSP1

<400> SEQUENCE: 11
caacaacccc cgtgcctacg cctactcccg ctcaccggga ccgtccattc ggacgtacga      60
gacccggtcc cggtgtagac gccacgaagg gagtagagag ggttgaccga ccagagacgg     120
cgtgtgacga tgtagctact gtctcctaag tccatgagtc tggggtgcgt cacctgccgg     180
aaggacccga acgtgctggt ctcggtcgcg tcgcggggac cccacgtcct cgcgtccgag     240
ttcgcgtagt agagggtggg gaagaagtta ctgaagtgga agctgatact gtagcgcgac     300
gacctcgacc tctttggccg tctcatgtcg aggtaccacg ccgggtagac ggacggcctg     360
cggagggtac agaagggacg gccgttccgg tagacccagt gcccgacccc tgtgtgggtc     420
atacctccgt gaccgcgcga ctaggacgtt ttcccactct aggcgcagta gttggtctgg     480
tggacgctct tggaggacgg cgtcgtctag tgcggcgcgt actacacgca cccgaaggag     540
tcgccgccgc acctgaggac ggtcccacta aggcccctg gggacaggtc gcacctccgc      600
ctacccgcct agaaggtccg gccacaccac tcgacccctc tgccgacgcg agtctccttg     660
ttcggtccgc acatgtgttc cgagggagac aaagccctga cctagtttct cttgtgaccc     720
catatc                                                                726
```

INHIBITORS OF SERINE PROTEASE ACTIVITY OF MATRIPTASE OR MTSP1

FIELD OF THE INVENTION

The present invention is directed to methods of reducing tumor progression and/or metastasis. Matriptase and MTSP1 are serine proteases reported to be expressed in high levels in certain cancer cell lines.

According to one aspect, the present invention provides compounds which bind to the serine protease domain and are active as selective inhibitors of the serine protease activity of matriptase or MTSP1. These inhibitors can be used to inhibit the serine protease activity of matriptase or MTSP1 and thereby reduce harmful effects of its overexpression. Another aspect of the present invention is directed to the use of compounds that bind to the serine protease domain and selectively inhibit the serine protease activity of matriptase or MTSP1; such compounds may be used in the prevention and treatment of cancerous conditions and which decrease the growth of cancerous tumors and retard metastasis.

BACKGROUND AND INTRODUCTION TO THE INVENTION

Cancer is the second leading cause of death in the United States, after heart disease (Boring, C. C. et al., 1993, CA Cancer J. Clin. 43:7), and develops in one in three Americans. One of every four Americans dies of cancer. Cancer is characterized primarily by an increase in the number of abnormal, or neoplastic, cells derived from a given normal tissue which proliferate to form a tumor mass, the invasion of adjacent tissues by these neoplastic tumor cells, and the generation of malignant cells which spread via the blood or lymphatic system to regional lymph nodes and to distant sites. The latter progression to malignancy is referred to as metastasis.

Cancer can be viewed as a breakdown in the communication between tumor cells and their environment, including their normal neighboring cells. Signals, both growth-stimulatory and growth-inhibitory, are routinely exchanged between cells within a tissue. Normally, cells do not divide in the absence of stimulatory signals, and likewise, will cease dividing in the presence of inhibitory signals. In a cancerous, or neoplastic, state, a cell acquires the ability to "Override" these signals and to proliferate under conditions in which normal cells would not grow.

Tumor cells must acquire a number of distinct aberrant traits to proliferate. Reflecting this requirement is the fact that the genomes of certain well-studied tumors carry several different independently altered genes, including activated oncogenes and inactivated tumor suppressor genes. Each of these genetic changes appears to be responsible for imparting some of the traits that, in aggregate, represent the full neoplastic phenotype (Land, H. et al. 1983, Science 222:771; Ruley, H. E., 1983, Nature 304:602; Hunter, T. 1991, cell 64:249).

In addition to unhindered cell proliferation, cells must acquire several traits for tumor progression to occur. For example, early on in tumor progression, cells must evade the host immune system. Further, as tumor mass increases, the tumor must acquire vasculature to supply nourishment and remove metabolic waste. Additionally, cells must acquire an ability to invade adjacent tissue, and, ultimately, cells often acquire the capacity to metastasize to distant sites.

A variety of biochemical factors have been associated with different phases of metastases. Cell surface receptors for collagen, glycoproteins such as laminin, or proteoglycans, facilitate tumor cell attachment, an important step in invasion and metastases. Attachment then triggers the release of degradative enzymes which facilitate the penetration of tumor cells through tissue barriers. Once the tumor cells have entered the target tissue, specific growth factors are required for further proliferation.

One of the major characteristics of cancer cells is their ability to invade surrounding normal tissues and metastasize to distant body sites. It is the metastatic nature of malignant tumors that presents a great challenge to clinicians in terms of treatment, since the tumor is no longer localized to one area.

Tumor invasion (or progression) is a complex series of events, in which tumor cells detach from the primary tumor, break down the normal tissue surrounding it, and migrate into a blood or lymphatic vessel to be carried to a distant site. The breaking down of normal tissue barriers is accomplished by the elaboration of specific enzymes that degrade the proteins of the extracellular matrix that make up basement membranes and stromal components of tissues.

A class of extracellular matrix degrading enzymes has been identified called the matrix metalloproteinases (MMP). Two of the matrix metalloproteinases have been implicated in tumor invasion. The type IV collagenase has been correlated with the metastatic potential of tumor cells. (Liotta, et al., *Nature*, 284:67–68 (March, 1980)). It has been reported that the production of the matrix metalloproteinase stromelysin was associated with malignant tumors with metastatic potential. (McDonnell and Matrisian, *Smnrs. in Cancer Biology* 1:107–115 (1990); McDonnell and Matrisian, *Cancer and Metastasis Reviews* 9:309–319 (1990).)

The capacity of cancer cells to metastasize and invade tissue is facilitated by degradation of the basement membrane. Several proteinase enzymes have been reported to facilitate the process of invasion of tumor cells. One family of enzymes, MMPs, has been implicated as enhancing degradation of the basement membrane to allow tumorous cells to invade tissues. MMPs have been reported to differ in molecular weight and antigenic properties. Previously, two major metalloproteinases having molecular weights of about 70 kDa and 92 kDa have been studied. Both of these MMPs have been reported to enhance ability of tumor cells to metastasize. Two natural inhibitors of these enzymes known as tissue inhibitors of metalloproteinase (TIMP) have been identified. The inactivated unclipped collagenases are generally secreted as a complex with TIMP. Enzymatic activity of the 72 kDa and 92 kDa proteins has been reported to depend on secreted ratios of collagenase/TIMP.

Matriptase is a trypsin-like serine protease which has been isolated and cloned from T-47D human breast cancer cells. Matriptase has been isolated from T-47D cell-conditioned medium. (Lin, et al., *J. Biol. Chem.* 274(26):18231–18236 (1999).) Upon analysis of the cDNA, it was determined that the protease had 683 amino acids and contained three main structural regions: a serine protease domain near the carboxyl-terminal region, four tandem low-density lipoprotein receptor domains, and two tandem complement subcomponents C1r and C1s. Matriptase was reported to be a mosaic protein with broad spectrum cleavage activity and two potential regulatory modules. It was named "matriptase" because of the ability of the protease to degrade the extra-cellular matrix and its trypsin-like activity. (Lin, et al., *J. Bio. Chem.* 274:18231–18236 (1999).)

Matriptase is reported to be a protease having activity in degrading extracellular matrix that is localized on the cell surface. When isolated from breast cancer cells (or T-47D cell conditioned medium), matriptase has been reported to be primarily in an uncomplexed form. Matriptase has been isolated from human milk. When isolated from human milk, matriptase was reported to be in one of two complexed forms, 95 kDa (the predominant form) and 110 kDa; uncomplexed matriptase was not detected. (Liu, et al., *J. Biol. Chem.* 274(26):18237–18242 (1999).) It has been proposed that matriptase exists as an uncomplexed protease when in its active state. In breast milk, matriptase has been reported to exist in complex with a fragment of hepatocyte growth factor inhibitor-1 (HAI-1), a Kuntz-type serine protease inhibitor having activity against trypsin-like serine proteases.

Ecotin and Ecotin M84R/M85R have been reported to be macromolecular inhibitors of serine proteases of the chymotrypsin fold and have been reported to inhibit ductal branching, morphogenesis and differentiation of the explanted ductal prostate. PC-3 is a cell line derived from prostate cancer epithelial cells. Ecotin and M84R/M85R ecotin were found to decrease tumor size and metastasis in PC-3 implanted nude mice. Studies to identify additional serine proteases made by cancer cells were done using PC-3 cells. By using PCR techniques and degenerate oligonucleotide primers, five independent serine protease cDNAs were reported isolated from PC-3 mRNA. A serine protease termed "MT-SP1" was cloned, its cDNA characterized and reported to encode a mosaic, transmembrane protease. (Takeuchi, et al., *PNAS* (US) 96:11054–11061 (1999).)

It was subsequently reported that the reported matriptase sequence was included in the translated sequence for the cDNA of MT-SP1. The matriptase cDNA was reported to be a partial MT-SP1 cDNA and to lack 516 of the coding nucleotides. (Takeuchi, et al., *J. Biol. Chem* 275:26333–26342 (2000).) Since the reported matriptase cDNA sequence encoded a possible initiating methionine, it was proposed that alternative splicing could yield a protein lacking the N-terminal region of MT-SP1.

Both matriptase and MT-SP1 are reported to demonstrate trypsin-like protease activity. MT-SP1 has been reported to be a Type II transmembrane protein with an extracellular protease domain. Studies on matriptase have reported that a portion of enzyme molecules were localized on the surfaces of cells.

Additional studies have investigated the substrate specificity of MT-SP1. These experiments have reported that protease-activated receptor 2 (PAR2) and single-chain urokinase-type plasminogen activator (sc-uPA) are macromolecular substrates of MT-SP1. PAR2 is reported to function in inflammation, cytoprotection and/or cell adhesion, while sc-uPa is reported to function in tumor cell invasion and metastasis.

Elevated proteolytic activity has been implicated in neoplastic progression. The role(s) of proteolytic enzymes, including serine proteases, in neoplastic progression are under study. Proteases have been proposed to contribute to the degradation of excellular matrix and to tissue remodeling and, thus, may assist in cancer invasion and metastasis.

A number of extracellular proteases have been reported and expression of some of these proteases has been said to correlate with tumor progression. (Mignatti, P. and Rifkin, D. B., *Physiol. Rev.* 73:161–195 (1993).)

SUMMARY OF THE INVENTION

In one aspect, the present invention relates to compounds which bind to the serine protease domain of matriptase or MTSP1 and which are selective inhibitors of the serine protease activity matriptase or MTSP1 and to their use in inhibiting the serine protease activity matriptase or MTSPI. As noted above, the reported sequence for MT-SP1 includes the reported matriptase sequence. We have cloned the serine protease domain and have determined that matriptase and MTSP1 have a common serine protease domain. Inhibition of serine protease activity of matriptase or MTSP1 is useful in the prevention and treatment of cancerous conditions, including having activity in retarding tumor progression and metastasis.

Matriptase and MTSP1 both have been reported to be trypsin-like serine proteases involved in the degradation of the extracellular matrix (ECM). Our cloning studies indicate that matriptase and MTSP1 share a common serine protease domain. Degradation of the extracellular matrix (basement membrane and interstitial stroma) is an important aspect of metastasis and is required for metastatic cancer cells to migrate through anatomical barriers and to invade tissues. Thus, breakdown of the extracellular matrix is a primary factor in progression of cancerous conditions. In one aspect, the present invention relates to compounds and their use for the selective inhibition of serine protease activity of matriptase or MTSP1 in order to decrease the cancer-related breakdown of the extracellular matrix.

The present invention is also directed to administration of a selective inhibitor of serine protease activity of matriptase or MTSP1 to an area of an animal suspected of having metastic cancer cells in order to retard tumor progression. Also, provided are pharmaceutical compositions which comprise a selective inhibitor of serine protease activity matriptase or MTSP1 and a pharmaceutically acceptable carrier.

The present invention also provides methods for the selection of the compounds that will selectively modulate the serine protease activity of matriptase or MTSP1.

Thus, according to one aspect of the present invention, provided are methods of detecting a compound which inhibits serine protease activity of matriptase or MTSP1 which comprises contacting said compound with a peptide comprising a recombinant serine protease domain derived from matriptase or MTSP1 and a substrate and measuring substrate hydrolysis. Preferably the serine protease domain comprises SEQ. ID. NO. 2 or an amino acid sequence having a serine protease activity and at least about 80% sequence identity to SEQ. ID. NO. 2. More preferably, the serine protease domain comprises an amino acid sequence having at least about 90%, even more preferably about 95% or more, sequence identity to SEQ. ID. NO. 2.

Alternatively, the present invention is directed to a method of screening a compound having activity in inhibiting serine protease activity of matriptase or MTSP1 which comprises determining whether said compound inhibits serine protease activity of a peptide comprising a recombinant serine protease domain derived from matriptase or MTSP1. Preferably said peptide comprises SEQ. ID. NO. 2 or an amino acid sequence having serine protease activity and at least about 80%, more preferably at least about 90%, and even more preferably 95% or more, sequence identity to SEQ. ID. NO. 2.

Also provided is a method of screening a compound for activity in inhibiting serine protease activity of matriptase or MTSP1 which comprises determining whether said compound inhibits activity of a peptide comprising a recombinant serine protease domain comprising SEQ. ID. NO. 2 or an amino acid sequence having serine protease activity and at least about 80% sequence identity to SEQ. ID. NO. 2. Preferably the amino acid sequence has at least about 90% sequence identity and more preferably 95% or more sequence identity to SEQ. ID. NO. 2.

According to a further aspect, the present invention provides a recombinant serine protease domain derived from matriptase or MTSP1 which comprises SEQ. ID. NO. 2 or an amino acid sequence having serine protease activity and at least about 80% sequence identity to SEQ. ID. NO. 2. Also provided is a recombinant serine protease domain which comprises SEQ. ID. NO. 2 or an amino acid sequence having serine protease activity and at least about 80% sequence identity to SEQ. ID. NO. 2. More preferably, the serine protease domain comprises an amino acid sequence having at least about 90% and more preferably about 95% or more sequence identity to SEQ. ID. NO. 2. Especially preferred is a serine protease domain which comprises SEQ. ID. NO. 2.

DEFINITIONS

"Matriptase" is a trypsin-like serine protease active in the development of cancerous conditions, such as tumors and metastasis of cancer. Matriptase is a matrix degrading protease that is reported to be localized on the cell surface. Matriptase is reported to have 683 amino acids and contains three main structural regions, a serine protease domain near the carboxyl-terminal region, four tandem low-density lipoprotein receptor domains, and two tandem complement subcomponents C1r and C1s.

Membrane-type serine protease 1 ("MT-SP1" or "MTSP1") refers to a serine protease originally cloned from the PC-3 cell line. MT-SP1 is reported to be a Type II transmembrane protein with an extracellular protease domain. The amino acid sequence reported for matriptase has been reported to be included within the translated sequence for the cDNA of MT-SP1. The cDNA of MT-SP1 is reported to have, in addition to regions coding for the three main structural regions described above for matriptase, an additional 516 nucleotides that make up a signal/anchor domain.

A "cancerous condition" is one in which the patient has a progressive human cancer, such as, leukemia, lymphomas, human melanomas, breast, gastrointestinal, such as esophageal, stomach, colon, bowel, colorectal and rectal cancers, prostate, bladder, testicular, ovarian, uterine, cervical, brain, lung, bronchial, larynx, pharynx, pancreatic, thyroid, bone, and various types of skin cancers.

A "tumor," also known as a neoplasm, is an abnormal growth of tissue resulting from uncontrolled cell replication, often related to cancer.

"Metastasis" is the spread of cancer from an original location to a new location in the body.

BRIEF DESCRIPTION OF THE FIGURES

FIGS. 1A to 1C depict certain preferred selective inhibitors of matriptase.

FIGS. 3A to 3C depict the nucleic acid sequences (SEQ. ID. NO. 1) and (SEQ. ID. NO. 11) and corresponding amino acid sequence (SEQ. ID. NO. 2) for a cDNA fragment encoding the entire serine protease domain of recombinant matriptase or MTSP1 (rMAP) cloned from the human adenocarcinoma cell line PC-3 as described in Example 1.

DETAILED DESCRIPTION OF THE INVENTION

1. Preferred Compounds

Figure 2A:
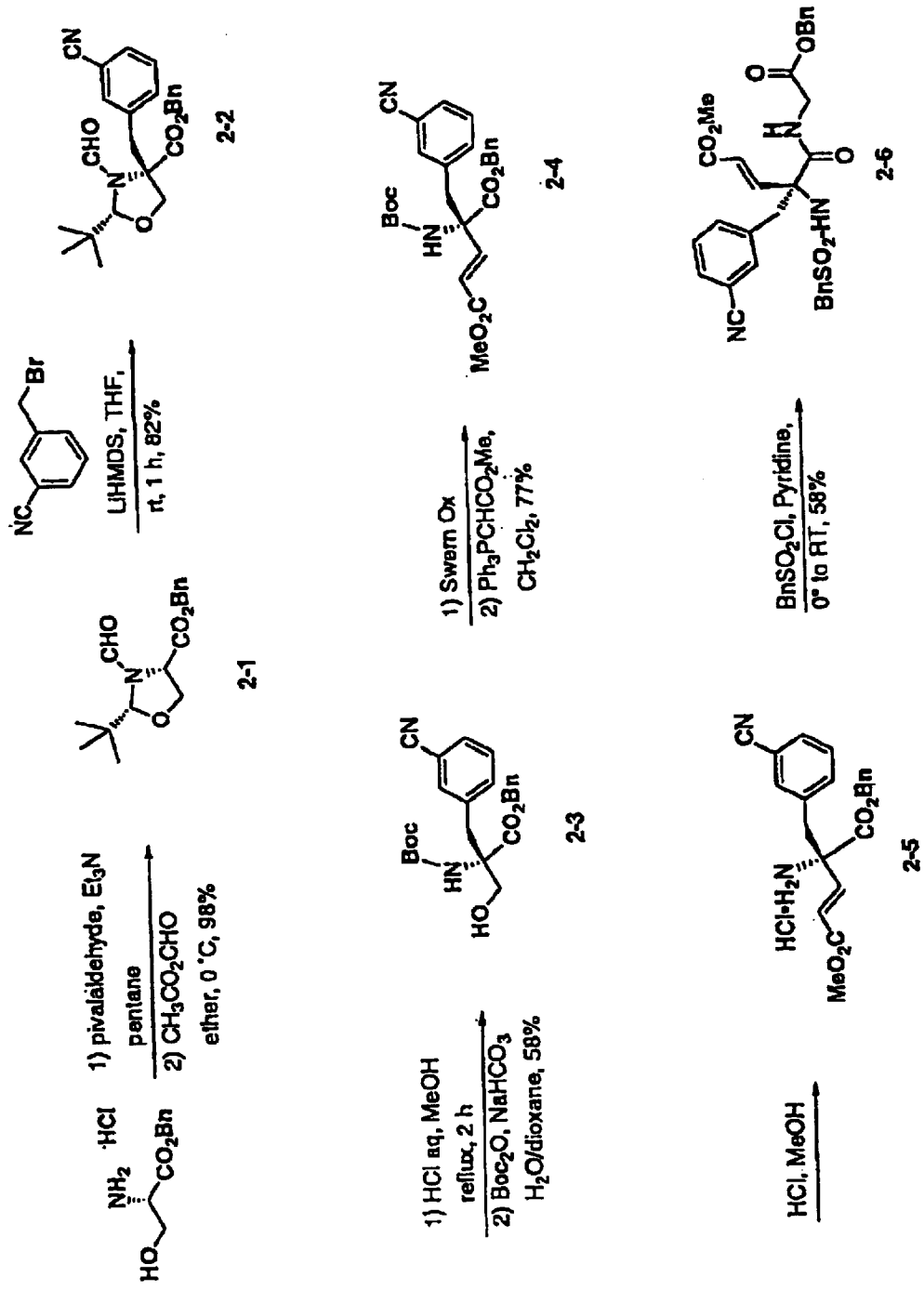
FIGS. 2A and 2B depict a synthetic scheme for the synthesis of compound 6 of FIG. 1A.

Suitable compounds for use according to the methods of the present invention are selected for their potency and selectivity in inhibiting serine protease activity of matriptase or MTSP1 while not significantly inhibiting activity of other serine proteases important for cellular homeostasis.

Preferred compounds for use according to the present invention include those which will selectively inhibit serine protease activity of matriptase or MTSP1 without substantially inhibiting circulating serine proteases, particularly serine proteases of the coagulation cascade, especially thrombin and factor Xa.

In one aspect, preferred are compounds which selectively inhibit the serine protease activity of matriptase or MTSP1 but which do not appreciably inhibit the activity of factor Xa or thrombin. More preferably, such compounds do not appreciably inhibit both factor Xa and thrombin. These compounds are characterized by having a $IC_{50}$ for either factor Xa or thrombin which is at least two times, and more preferably five times greater, than its $IC_{50}$ for inhibiting serine protease activity of matriptase or MTSP1. Preferably, the compound will have an $IC_{50}$ for each of factor Xa and thrombin at least two times and more preferably five times or greater than its $IC_{50}$ for matriptase or MTSP1. More preferred are those compounds having an $IC_{50}$ for each of factor Xa and thrombin that is at an order of magnitude (10 times) higher than the $IC_{50}$ for serine protease activity of matriptase or MTSP1. More preferred are those compounds which also do not appreciably inhibit plasmin, and which are characterized by having an $IC_{50}$ for plasmin which is at least two times, more preferably five times, their $IC_{50}$ for serine protease activity of matriptase or MTSP1. These compounds are believed to be useful either as in vitro diagnostic agents for selectively inhibiting serine protease activity of matriptase or MTSP1 while only weakly inhibiting, if at all, factor Xa, thrombin and/or plasmin or as pharmacological agents for the treatment of pathologic disorders characterized by over-expression and/or over-activity of serine protease activity matriptase or MTSP1.

According to an alternate aspect of the present invention, preferred compounds include compounds which inhibit serine protease activity of matriptase or MTSP1 by a non-covalent mode of action.

Figure 1A:
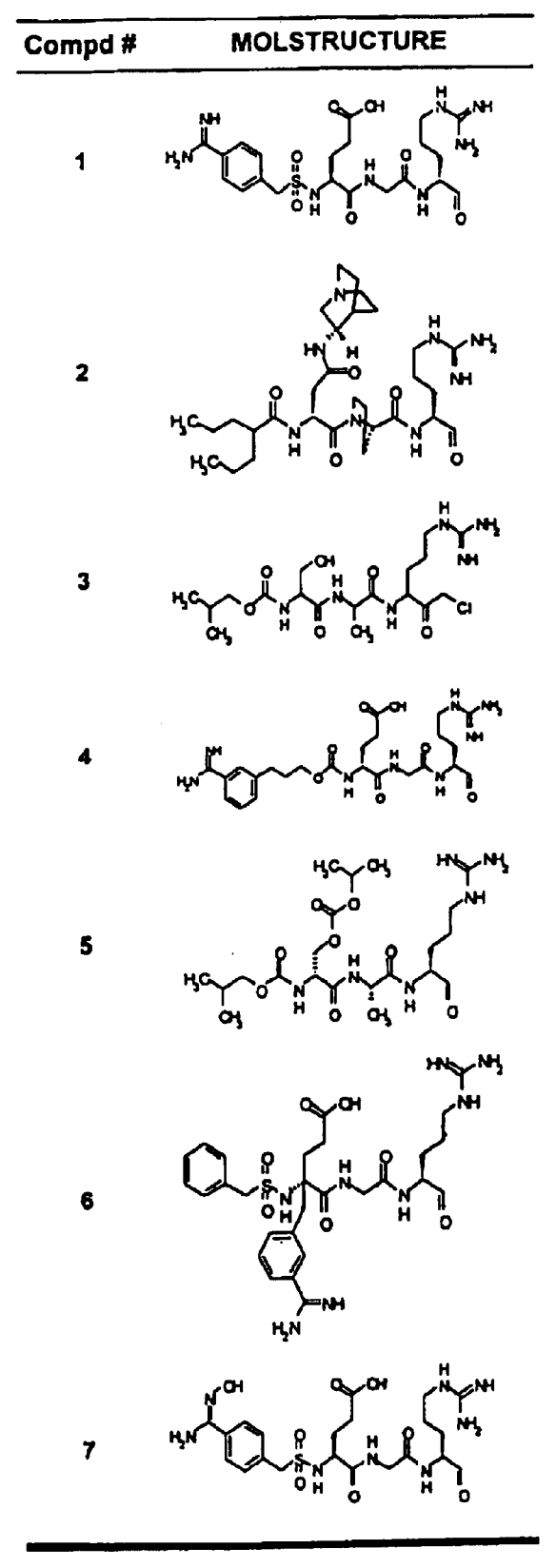
Figure 1B:
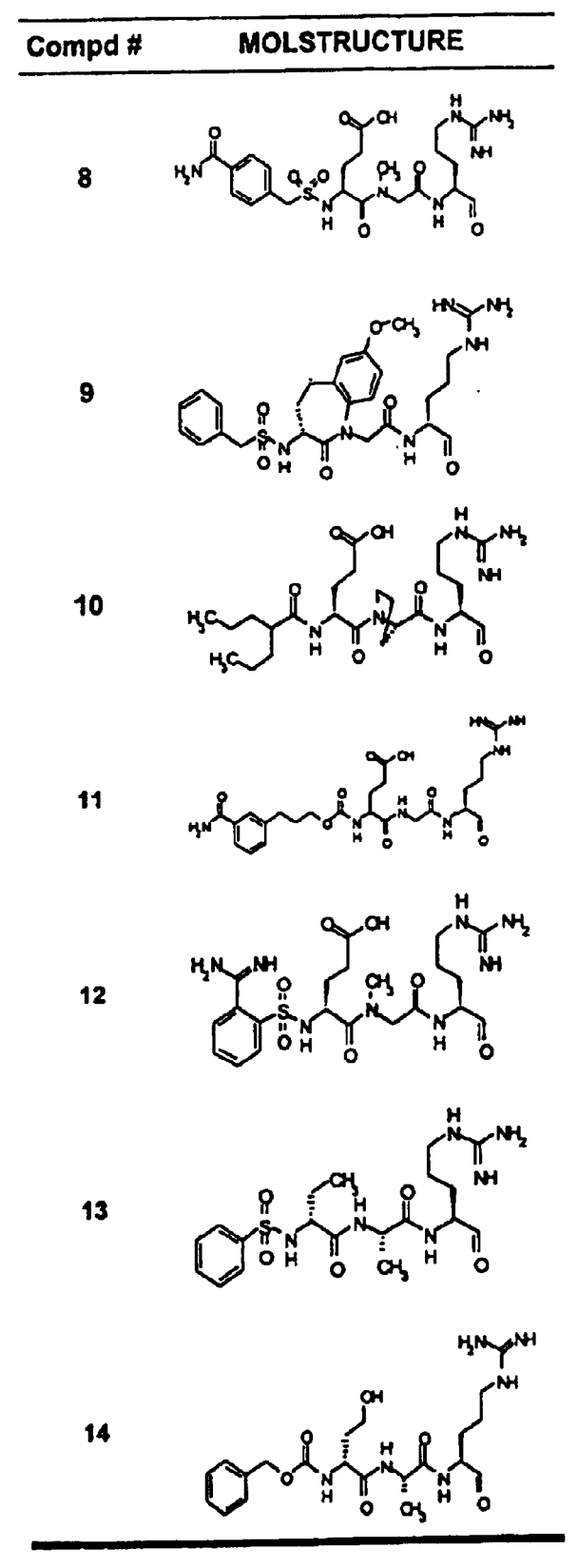
Figure 1C:
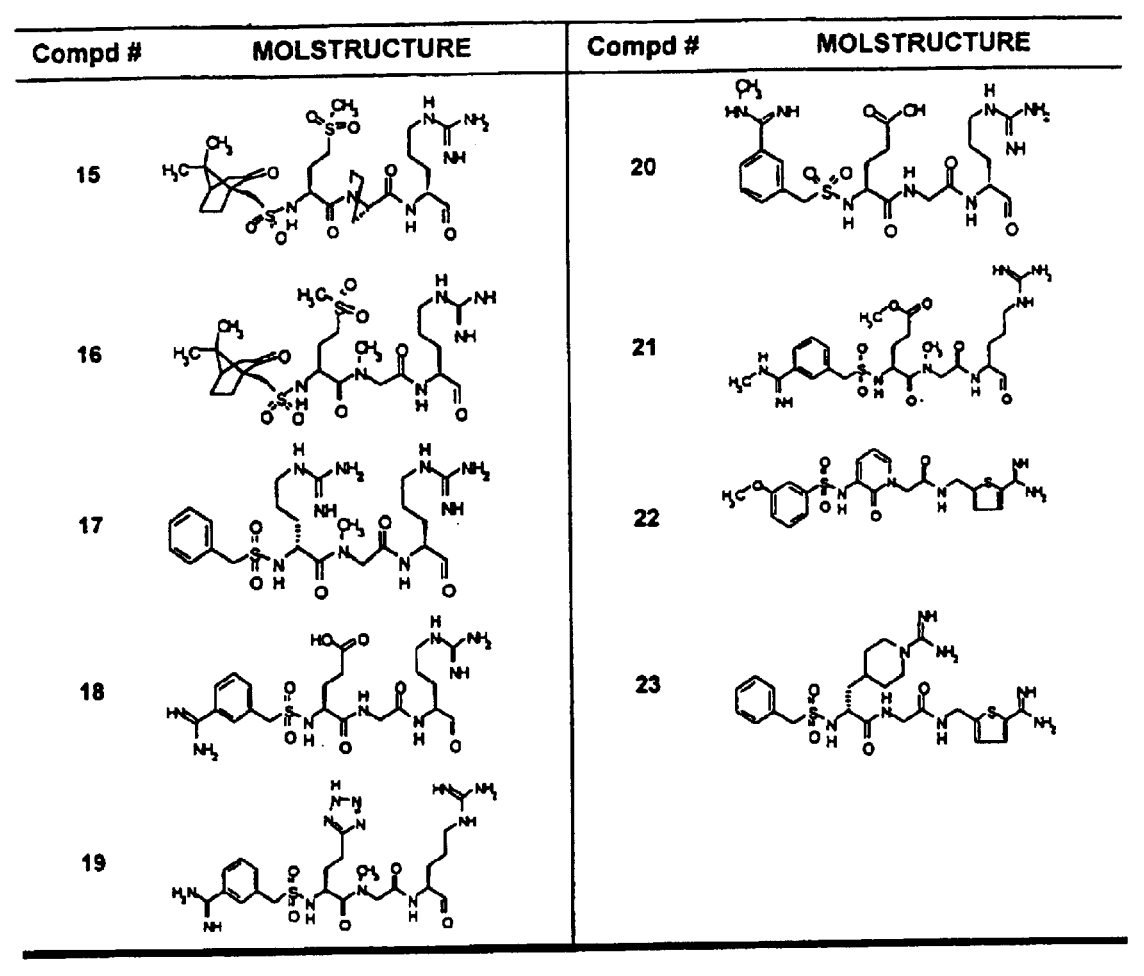

Preferred compounds which are inhibitors of serine protease activity matriptase or MTSP1 include those depicted in FIGS. 1A to 1C.

2. Preparation of the Preferred Compounds

Certain of the preferred compounds of the present invention may be conveniently prepared by following the synthetic methods and techniques described in U.S. Pat. Nos. 5,492,895; 5,534,498, 5,955,976; 5,646,195; 5,658,939; 5,696,231; 5,681,844; 5,703,208; 5,714,499; 5,731,413; 5,739,112; 5,770,600; 5,775,927; 5,883,077; 5,886,146; 6,034,215; 6,025,472; WO 00/05245; and Tamura, et al., *Bioorganic & Medicinal Chemistry Letters* 9:2573–2578 (1999), the disclosures of which are incorporated by reference herein.

Figure 2B:
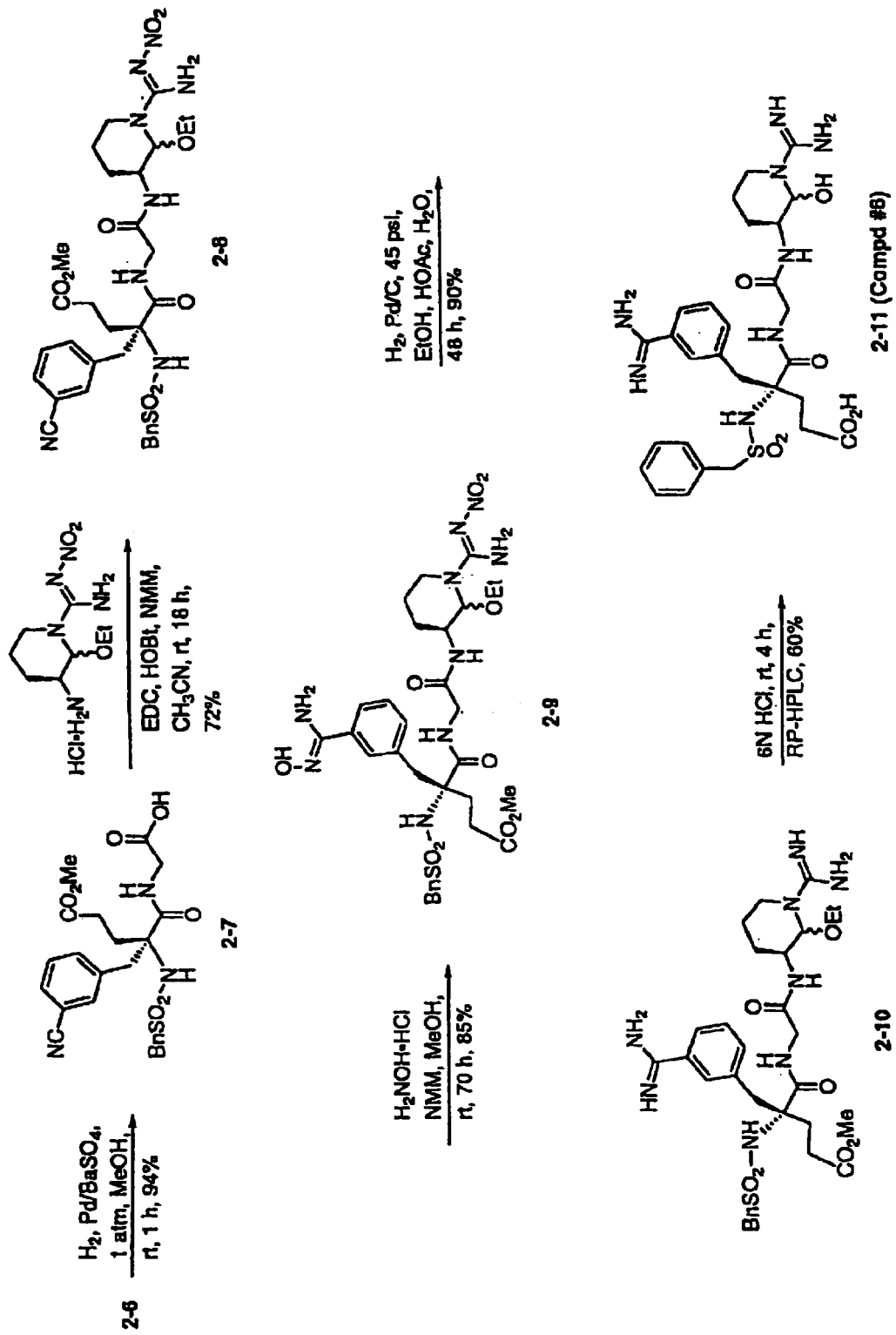

FIGS. 2A and 2B depict a synthetic scheme for the preparation of Compound No. 6 of FIG. 1A.

3. Selection of Preferred Compounds

According to one aspect of the present invention, preferred compounds of the present invention are selected for their potency and selectivity in inhibiting serine protease activity of matriptase or MTSP1. As described in Examples A and B, and as is generally known, a target serine protease and its substrate are combined under assay conditions permitting reaction of the protease with its substrate. The assay is performed in the absence of a test compound, and in the presence of increasing concentrations of the test compound. The concentration of test compound at which 50% of the serine protease activity is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the serine protease than those compounds having higher $IC_{50}$ or $EC_{50}$ values. The $IC_{50}$ measurement is often used for more simplistic assays, whereas the $EC_{50}$ is often used for more complicated assays, such as those employing cells.

Preferred compounds according to this aspect of the present invention have an $IC_{50}$ value of 100 nM or less as measured in an in vitro assay for inhibition of serine protease activity of matriptase or MTSP1 activity. Especially preferred compounds have an $IC_{50}$ value of less than 30 nM.

The test compounds also are evaluated for selectivity toward inhibiting serine protease activity of matriptase or MTSP1 in relation to other serine proteases (see Examples A and B). As described in the Examples, and as generally known, a test compound is assayed for its potency toward a panel of serine proteases and other enzymes and an $IC_{50}$ value or $EC_{50}$ value is determined for each test compound in each assay system. A compound that demonstrates a low $IC_{50}$ value or $EC_{50}$ value for the target enzyme, e.g., the serine protease domain of matriptase or MTSP1, and a higher $IC_{50}$ value or $EC_{50}$ value for other enzymes within the test panel (e.g., tissue plasminogen activator, thrombin, Factor Xa), is considered to be selective toward the target enzyme. Generally, a compound is deemed selective if its $IC_{50}$ value or $EC_{50}$ value in the target enzyme assay is less than one half, preferably one-fifth and more preferably one order of magnitude less than the next smallest $IC_{50}$ value or $EC_{50}$ value measured in the selectivity panel of enzymes.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of the compound of the present invention can range broadly depending upon the desired effects and the therapeutic indication. Typically, dosages will be between about 0.01 mg/kg and 100 mg/kg body weight, preferably between about 0.01 and 10 mg/kg body weight.

Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

5. Utility

The compounds of the present invention have matriptase inhibitory activity.

The compounds of the present invention are active as inhibitors of matriptase and specifically bind matriptase. More particularly, preferred compounds bind to the serine protease domain of matriptase and inhibit its activity.

It is believed that these compounds will be useful in the prevention or treatment of cancerous conditions where that cancerous condition is exacerbated by the activity of matriptase.

Another use for the compounds of the present invention is to decrease progression of cancerous conditions and the concomitant degradation of the cellular matrix.

The compounds of the present invention are active as inhibitors of serine protease activity of matriptase or MTSP1 and specifically bind to the serine protease domain of matriptase or MTSP1. Accordingly, those compounds that contain sites suitable for linking to a solid/gel support may be used in vitro for affinity chromatography to purify matriptase from a sample or to remove matriptase from a sample using conventional affinity chromatography procedures. These compounds are attached or coupled to an affinity chromatography either directly or through a suitable linker support using conventional methods. See, e.g. Current Protocols in Protein Science, John Wiley & Sons (J. E. Coligan et al., eds, 1997) and Protein Purification Protocols, Humana Press (S. Doonan, ed., 1966) and references therein.

The compounds of the present invention having matriptase or MTSP1 serine protease inhibitory activity are useful in in vitro assays to measure matriptase or MTSP1 activity and the ratio of complexed to uncomplexed matriptase or MTSP1 in a sample. These assays could also be used to monitor matriptase or MTSP1 activity levels in tissue samples, such as from biopsy or to monitor matriptase activities and the ratio of complexed to uncomplexed matriptase for any clinical situation where measurement of matriptase or MTSP1 activity is of assistance. An assay which determines serine protease activity in a sample could be used in combination with an ELISA which determines total amount of matriptase or MTSP1 (whether complexed or uncomplexed) in order to determine the ratio of complexed to uncomplexed matriptase.

Various animal models can be used to evaluate the ability of a compound of the present invention to reduce primary tumor growth or to reduce the occurrence of metastasis. These models can include genetically altered rodents (transgenic animals), transplantable tumor cells originally derived from rodents or humans and transplanted onto syngenic or immuno-compromised hosts, or they can include specialized models, such as the CAM model described below, designed to evaluate the ability of a compound or compounds to inhibit the growth of blood vessels (angiogensis) which is believed to be essential for tumor growth. Other models can also be utilized.

Appropriate animal models are chosen to evaluate the in vivo anti-tumor activity of the compounds described in this invention based on a set of relevant criteria. For example, one criterion might be expression of matriptase or MTSP1 and/or matriptase or MTSP1 mRNA by the particular tumor being examined. Two human prostate derived tumors that meet this criterion are the LnCap and PC-3 cell lines. Another criterion might be that the tumor is derived from a tissue that normally expresses high levels of matriptase or MTSP1. Human colon cancers meet this criterion. A third criterion might be that growth and/or progression of the tumor is dependent upon processing of a matriptase or MTSP1 substrate (e.g., sc-u-PA). The human epidermoid cancer Hep-3 fits this criterion. Another criterion might be that growth and/or progression of the tumor is dependent on a biological or pathological process that requires matriptase or MTSP1 activity. Another criterion might be that the particular tumor induces expression of matriptase or MTSP1 by surrounding tissue. Other criteria may also be used to select specific animal models.

Once appropriate tumor cells are selected, compounds to be tested are administered to the animals bearing the selected tumor cells, and subsequent measurements of tumor size and/or metastatic spread are made after a defined period of growth specific to the chosen model.

The CAM model (chick embryo chorioallantoic membrane model), first described by L. Ossowski (J. Cell Biol. 107:2437–2445, 1988), provides another method for evaluating the anti-tumor and anti-angiogenesis activity of a compound.

Tumor cells of various origins can be placed on 10 day old CAM and allowed to settle overnight. Compounds to be tested can then be injected intravenously as described by Brooks, et al. (Methods in Molecular Biology 129:257–269, 1999). The ability of the compound to inhibit tumor growth or invasion into the CAM is measured 7 days after compound administration.

When used as a model for measuring the ability of a compound to inhibit angiogensis, a filter disc containing angiogenic factors, such as basic fibroblast growth factor (bFGF) or vascular ediothelial cell growth factor (VEGF), is placed on a 10 day old CAM as described by Brooks, et al. (Methods in Molecular Biology 129:257–269, 1999). After overnight incubation, compounds to be tested are then administered intravenously. The amount of angiogenesis is measured by counting the amount of branching of blood vessels 48 hours after the administration of compound (Methods in Molecular Biology 129:257–269, 1999).

The compounds of the present invention are useful in vivo for treatment of pathologic conditions which would be ameliorated by decreased serine protease activity of matriptase or MTSP1.

It is believed these compounds will be useful in decreasing or inhibiting metastasis, and degradation of the extracellular matrix in tumors and other neoplasms. These compounds will be useful as therapeutic agents in treating conditions characterized by pathological degradation of the extracellular matrix, including those described hereinabove in the Background and Introduction to the Invention.

The present invention includes methods for preventing or treating a condition in a mammal suspected of having a condition which will be attenuated by inhibition of serine protease activity of matriptase or MTSP1 comprising administering to said as mammal a therapeutically effective amount of a compound which selectively inhibits serine protease activity of matriptase or MTSP1or a pharmaceutical composition of the present invention.

The compounds of the present invention are administered in vivo, ordinarily in a mammal, preferably in a human. In employing them in vivo, the compounds can be administered to a mammal in a variety of ways, including orally, parenterally, intravenously, subcutaneously, intramuscularly, colonically, rectally, nasally or intraperitoneally, employing a variety of dosage forms.

In practicing the methods of the present invention, the compounds of the present invention are administered alone or in combination with one another, or in combination with other therapeutic or in vivo diagnostic agents.

As is apparent to one skilled in the medical art, a "therapeutically effective amount" of the compounds of the present invention will vary depending upon the age, weight and mammalian species treated, the stage of the disease or pathologic condition being treated, the particular compounds employed, the particular mode of administration and the desired effects and the therapeutic indication. Because these factors and their relationship to determining this amount are well known in the medical arts, the determination of therapeutically effective dosage levels, the amount necessary to achieve the desired result of inhibiting matriptase or MTSP1 serine protease activity, will be within the ambit of one skilled in these arts. Typically, administration of the compounds of the present invention is commenced at lower dosage levels, with dosage levels being increased until the desired effect of inhibiting matriptase or MTSP1 activity to the desired extent is achieved, which would define a therapeutically effective amount. For the compounds of the present invention such doses are between about 0.01 mg/kg and about 100 mg/kg body weight, preferably between about 0.01 and about 10 mg/kg body weight.

6. Screening Methods

According to an alternate aspect, the present invention provides a recombinant serine protease domain derived from matriptase or MTSP1. Examples 1 and 2 describe cloning and expression of a recombinant serine protease domain derived from matriptase or MTSP1 ("rMAP") using recombinant methods. Example A describes the use of rMAP in an amidolytic assay to test compounds for activity in inhibiting serine protease activity of matriptase or MTSP1. Suitable recombinant serine protease domains according to the present invention include peptides which comprise SEQ. ID. NO. 2 or an amino acid sequence having serine protease activity and at least about 80% sequence identity to SEQ. ID. NO. 2. Such sequences include allelic variants and sequences having single nucleotide polymorphisms, but which result in peptides having serine protease activity.

Sequence identity of an amino acid sequence to a reference amino acid sequence (such as SEQ. ID. NO. 2) may be determined by techniques known to those skilled in the art. In making a determination regarding sequence identity, an alignment of the peptides to be compared is made. Such an alignment may be made manually or using certain algorithms developed for such use which are conventionally used. A comparison of residues occupying analogous positions is then made and the number of identical residues is scored.

Peptides which comprise a recombinant serine protease domain derived from matriptase or MTSP1 are useful in screening compounds for activity in inhibiting serine protease activity of matriptase or MTSP1. Use of one such peptide (rMAP) in an amidolytic assay is described in Example A.

To assist in understanding, the present invention will now be further illustrated by the following examples. These examples as they relate to this invention should not, of course, be construed as specifically limiting the invention and such variations of the invention, now known or later developed, which would be within the purview of one skilled in the art and which are considered to fall within the scope of the invention as described herein and hereinafter claimed.

EXAMPLES

Example 1

Isolation and Cloning of Matriptase

A. Cell Type and Growth of Cells

Human prostate adenocarcinoma cell line, PC-3, was purchased from ATCC (catalog number CRL-1435; Manassas, Va.). The cells were cultured at 37° C., 5% $CO_2$ in Ham's F-12K growth medium (catalog number 9077; Irvine) supplemented with 2 mM. L-glutamine and 10% fetal bovine serum. All subsequent cell manipulations were carried out according to the manufacturer's instructions. PC-3 cells were allowed to grow to about 90% confluence, and were then washed briefly with 1x phosphate buffered saline.

B. Isolation of Total RNA, and Purification and Enrichment of PolyA$^+$ RNAs

PC-3 cells were lysed in Trizol reagent (catalog number 15596; Life Technologies, Rockville, Md.) and total RNA was isolated according to the manufacturer's protocol. The concentration of total RNA was estimated from absorbance reading 260 nm. PolyA$^+$ RNAs were purified and enriched using oligo-dT beads (catalog number 70061; Oligotex, Qiagen, Valencia, Calif.).

C. Reverse-transcription and Polymerase Chain Reaction (PCR)

PC-3-derived polyA$^+$ RNAs were converted to single-stranded cDNA (sscDNA) by reverse transcription using ProSTAR first-strand RT-PCR kit (catalog number 200420; Stratagene, La Jolla, Calif.) and SuperScript II RNase H$^-$ reverse transcriptase (catalog number 18064-022; Life Technologies). After reverse transcription, an aliquot of PC-3 sscDNA (4 µL) was subjected to PCR using 2 mM each of the sense and anti-sense degenerate oligonucleotide primers and Taq polymerase (catalog number 201203; Qiagen). Total reaction volume was 100 µL. The sequence of the sense primer was 5'TGGRT(I)VT(I)WS(I)GC(I)RC(I)CAYTG-3' (SEQ. ID. NO. 3), and that of the anti-sense was 5'-(I)GG(I)CC(I)CC(I)SWRTC(I)CCYT(I)RCA(I)GHRTC-3' (SEQ. ID. NO. 4), where R=A,G; V=G,A,C; W=A,T; S=G,C; Y=C,T; H=A,T,C. The primer sequences correspond to two highly conserved regions in all (chymo)trypsin-like serine proteases and amplify PCR products ranging from approximately 400 to 500 base pairs.

D. Clone Screening and Sequencing

The PCR products were separated on a 2% agarose gel and purified using a gel extraction kit (catalog number 28706; QIAquick gel extraction kit; Qiagen). The purified DNA fragments were ligated into pCR2.1-TOPO (catalog number K4500-01; Invitrogen, Carlsbad, Calif.). After transformation into E. coli cells, plasmid DNAs were isolated and analyzed by digestion with EcoRI restriction enzyme. Clones that had insert DNAs were further characterized by sequencing using a fluorescent dye-based DNA sequencing method (catalog number 4303149; BigDye terminator cycle sequencing kit with AmpliTaq DNA polymerase; Perkin Elmer, Lincoln, Calif.). A total of 31 clones were sequenced and analyzed. All sequences were analyzed by a multiple nucleotide sequence alignment algorithm (blastn) (www.ncbi.nlm.nih.gov/blast) to identify identical or closely related cDNAs deposited in GenBank (NCBI, Bethesda, Md.). Those that did not show significant homology were further analyzed using blastx, which compares the six-frame conceptual translation products of a nucleotide sequence (both strands) against a protein sequence database (SwissProt). Eight clones yielded identical cDNA fragments that encode a novel serine protease, whose sequence did not match 100% to any deposited sequence at that time. This novel serine protease was named MTSP1. The closest match found was with the mouse epithin mRNA (85% identity; GenBank accession number AF042822) which encodes a membrane-type serine protease, and the human SNC19 mRNA (98% identity; GenBank accession number HSU204, 28) which contains a partial sequence of MTSP1. MTSP1 was subsequently found to be identical to matriptase (GenBank accession number AF118224) whose sequence appeared in GenBank after the cDNA encoding MTSP1 had been cloned and sequenced at Corvas.

E. Rapid Amplification of cDNA Ends (RACE) and Gene-specific Amplification of MTSP1

To obtain a cDNA encoding the complete protease domain of MTSP1, both RACE and gene-specific amplification reactions were performed. Since the presence of the transcript was detected in prostate, a human prostate Marathon-Ready cDNA (catalog # 7418-1; Clontech) was used to isolate part of the cDNA encoding MTSP1. Marathon-Ready cDNAs are prepared to contain a known hybridization sequence at both the 5' and 3' ends of the sscDNA and are therefore specifically suited for the RACE reactions. The 3' region of MTSP1 cDNA was successfully obtained by a 3'-RACE reaction using a gene specific primer, 5'-CACCCCTTCTTCAATGACTTCACCTTCG-3' (SEQ. ID. NO. 5). The 5' end of the MTSP1 protease domain was obtained by gene-specific amplification reaction using two MTSP1-specific primers, 5'-TACCTCTCCTAC GACTCC-3' (SEQ. ID. NO. 6) for the sense primer and 5'-GAGGTTCTCGCAGGTGGTCTGGTTG-3' (SEQ. ID. NO. 7) for the antisense primer. The sequences for these two primers were obtained from the human SNC19 mRNA sequence. Both 3'-RACE reaction and gene-specific PCR produced DNA fragments that were >1 kbp in size. These fragments were subcloned into pCR2.1-TOPO. After transformation into E. coli cells, plasmid DNAs were isolated and analyzed by digestion with EcoRI restriction enzyme. Clones that had insert DNAs were characterized by Southern blot analysis (using the internal cDNA fragment as probe) and by DNA sequence analysis.

F. PCR Amplification of cDNA Encoding Full-length Protease Domain of MTSP1

To obtain a cDNA fragment encoding the entire protease domain of MTSP1, an end-to-end PCR amplification using gene-specific primers was used. The two primers used were: 5'-CTCGAGAAAAGAGTTGTTGGGGGCACGGATGCGGATGAG-3' (SEQ. ID. NO. 8) for the 5' end and 5'-GCGGCCGCACTATACCCCAGTGTTCTCTTTGATCCA-3' (SEQ. ID. NO. 9) for the 3' end. The 5' primer contained the sequence (underlined) that encodes the start of the MTSP1 protease domain (VVGGTDADE) (SEQ. ID. NO. 10). The 3' primer contained the stop codon (underlined) of MTSP1. A ~800-bp fragment was amplified, purified and subcloned into the *Pichia pastoris* expression vector, pPIC9K, resulting in pPIC9K-MTSP1.

G. Gene Expression Profile of MTSP1 in Normal Tissues, Cancer Cells and Cancer Tissues To obtain information regarding the tissue distribution and gene expression level of MTSP1, the DNA insert from pPIC9K-MTSP1 was used to probe a blot containing RNA from 76 different human tissues (catalog number 7775-1; human multiple tissue expression (MTE) array; CLONTECH, Palo Alto, Calif.). Significant expression was observed in the colon (ascending, transverse and descending), rectum, trachea, esophagus and duodenum. Moderate expression levels were observed in the jejunum, ileum, ilocecum, stomach, prostate, pituitary gland, appendix, kidney, lung, placenta, pancreas, thyroid gland, salivary gland, mammary gland, fetal kidney, and fetal lung. Lower expression levels were seen in the spleen, thymus, peripheral blood leukocyte, lymph node, bone marrow, bladder, uterus, liver, adrenal gland, fetal heart, fetal liver, fetal spleen, and fetal thymus. A significant amount of the MTSP1 transcript was also detected in colorectal adenocarcinoma cell line (SW480), Burkitt's lymphoma cell line (Daudi), and leukemia cell line (HL-60). RT-PCR of the MTSP1 transcript in several human primary tumors xenografted in athymic nude mice was performed using gene-specific primers. A high level of MTSP1 transcript was detected in colon adenocarcinoma (CX-1) and pancreatic adenocarcinoma (GI-103). Moderate levels were observed in another colon adenocarcinoma (GI-112), ovarian carcinoma (GI-102), lung carcinoma (LX-1), and breast carcinoma (GI-101). Another lung carcinoma (GI-117) expressed a low level of the MTSP1 transcript. A similar RT-PCR was performed to detect the presence of the MTSP1 transcript in PC-3 and LNCaP cell lines. Both cell lines expressed significant amounts of MTSP1 transcript.

H. Sequence Analysis

Figure 3C:
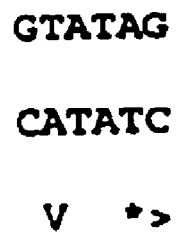

All derived DNA and protein sequences were analyzed using MacVector (version 6.5; Oxford Molecular Ltd., Madison, Wis.). The cDNA encoding the protease domain of MTSP1 is composed of 726 base pairs which translate into a 241-amino acid protein sequence (rMAP). See FIGS. 3A to 3C.

Example 2

Production of Recombinant Serine Protease Domain of Matriptase or MTSP1 (rMAP)

A. Fermentation

The production of multi-milligram amounts of rMAP was carried out by fermentation in a BioFlo 3000 fermentor (New Brunswick Scientific, N.J.) equipped with a 3.3 L capacity bioreactor using a SMD1168/pPIC9K:MTSP1 Sac SC1 clone. ZA001 complex media (10 g/L yeast extract, 20 g/L peptone, 40 g/L glycerol, 5 g/L ammonium sulfate, 0.2 g/L calcium sulfate dihydrate, 2 g/L magnesium sulfate heptahydrate, 2 g/L potassium sulfate, 25 g/L sodium hexametaposphate, 4.35 ml/L PTM1) was inoculated with 100 ml of an overnight culture of the *P. pastoris* transformant. The culture was supplemented with 50% glycerol by fed-batch phase and induced for 18–24 hours with methanol controlled at 0.025%.

B. Purification of Recombinant Serine Protease Domain of Matriptase or MTSP1 (rMAP)

The rMAP was secreted into the culture media, so the first step of the purification involved the removal of cells and cell debris by centrifugation at 5000 g for 30 minutes. The resulting supernatant was decanted, adjusted to pH 8.0 with 10N NaOH, and filtered through a SartoBran 300 0.45+0.2 $\mu$M capsule. This supernatant was concentrated to 1 L by ultrafiltration using a 10 kDa ultrafiltration cartridge (NC SRT UF system with AG/Technologies UFP-10-C-5A filter), and the buffer was exchanged by crossflow filtration into 50 mM tris-HCl, 50 mM NaCl, 0.05% tween-80, pH 8.0 (buffer A). The filtration unit was rinsed once with 1 L buffer A which was combined with the concentrate.

The concentrated rMAP-containing solution was passed over a 150 ml benzamidine column that had been equilibrated with buffer A, at a flow rate of 8 ml/min. The column was washed with 3 column volumes of 50 mM tris-HCl, 1.0M NaCl, 0.05% tween-80, pH 8.0 (buffer B) and eluted with 3 column volumes of 50 mM tris-HCl, 1.0M L-arginine, 0.05% tween-80, pH 8.0 (buffer C). Fractions containing rMAP were identified by activity assay and pooled. This pooled material was concentrated to 10 ml using a Jumbosep concentrator (Pall Gelman) and a 10 kDa cutoff membrane. Once concentrated to 10 ml, the buffer was exchanged into 50 mM $Na_2HPO_4$, 125 mM NaCl, pH 5.5 (buffer D) and the volume adjusted to 5–10 ml. The retentate was removed and the concentrator washed with buffer D which was added to the concentrate. The total sample volume was adjusted 15 ml.

The partially purified rMAP was passed through a 5 ml Q-sepharose Fast Flow HiTrap column (Amersham-Pharmacia Biotech) pre-equilibrated with 15 ml of buffer D. The flow through was collected. The HiTrap column was washed with an additional 10 ml of buffer D. Both flow throughs were pooled, and the protein concentration was determined by measurement of $OD_{280}$ (using an extinction coefficient of 2.012 mg/$OD_{280}$). Purified rMAP was then deglycosylated by the addition 0.1 $\mu$l of Endoglycosidase H (ProZyme, 5 U/ml) per mg of protein and incubating overnight at 4° C. with gentle swirling.

The conductivity of the deglycosylated pool was adjusted to 2.0–3.0 mS/cm with Nanopure $H_2O$ and the pH adjusted to 6.5 (~200–300 mL final volume). The rMAP was then further purified by anion exchange chromatography by loading directly onto a Pharmacia Akta Explorer system using a 7 mL Source 15Q anion exchange column (Amersham-Pharmacia Biotech). The protein was eluted in a buffer containing 50 mM HEPES, pH 6.5 with a 0–0.33M NaCl gradient over 10 column volumes at a flow rate of 6 ml/min. Fractions containing protein were pooled, and benzamidine was added to a final concentration of 10 mM. Protein purity was examined by SDS-PAGE and protein concentration determined by measurement of $OD_{280}$ and use of a theoretical extinction coefficient of 2.012 mg/$OD_{280}$.

Example A

Amidolytic Assay for Determining Inhibition of Serine Protease Activity of Matriptase or MTSP1

The ability of the compounds of the present invention to act as inhibitors of rMAP catalytic activity was assessed by determining the inhibitor-induced inhibition of amidolytic activity by the MAP, as measured by $IC_{50}$ values.

The assay buffer was HBSA (10 mM Hepes, 150 mM sodium chloride, pH 7.4, 0.1% bovine serum albumin). All reagents were from Sigma Chemical Co. (St. Louis, Mo.), unless otherwise indicated.

Two $IC_{50}$ assays (a) one at either 30-minutes or 60-minutes (a 30-minute or a 60-minute preincubation of test compound and enzyme) and (b) one at 0-minutes (no preincubation of test compound and enzyme) were conducted. For the $IC_{50}$ assay at either 30-minutes or 60-minutes, the following reagents were combined in appropriate wells of a Corning microtiter plate: 50 microliters of HBSA, 50 microliters of the test compound, diluted (covering a broad concentration range) in HBSA (or HBSA alone for uninhibited velocity measurement), and 50 microliters of the rMAP (Corvas International) diluted in buffer, yielding a final enzyme concentration of 250 pM as determined by active site filtration. Following either a 30-minute or a 60-minute incubation at ambient temperature, the assay was initiated by the addition of 50 microliters of the substrate S-2765 (N-α-Benzyloxycarbonyl-D-arginyl-L-glycyl-L-arginine-p-nitroaniline dihydrochloride; DiaPharma Group, Inc.; Franklin, Ohio) to each well, yielding a final assay volume of 200 microliters and a final substrate concentration of 100 µM (about 4-times $K_m$). Before addition to the assay mixture, S-2765 was reconstituted in deionized water and diluted in HBSA. For the $IC_{50}$ assay at 0 minutes; the same reagents were combined: 50 microliters of HBSA, 50 microliters of the test compound, diluted (covering the identical concentration range) in HBSA (or HBSA alone for uninhibited velocity measurement), and 50 microliters of the substrate S-2765. The assay was initiated by the addition of 50 microliters of rMAP. The final concentrations of all components were identical in both $IC_{50}$ assays (at 30- or 60- and 0-minute).

The initial velocity of chromogenic substrate hydrolysis was measured in both assays by the change of absorbance at 405 nM using a Thermo Max® Kinetic Microplate Reader (Molecular Devices) over a 5 minute period, in which less than 5% of the added substrate was utilized. The concentration of added inhibitor, which caused a 50% decrease in the initial rate of hydrolysis was defined as the respective $IC_{50}$ value in each of the two assays (30- or 60-minutes and 0-minute).

Example B

In Vitro Enzyme Assays for Specificity Determination

The ability of compounds to act as a selective inhibitor of matriptase activity was assessed by determining the concentration of test-compound which inhibited the activity of matriptase by 50%, ($IC_{50}$) as described in Example A, and comparing $IC_{50}$ value for matriptase to that determined for all or some of the following serine proteases: thrombin, recombinant tissue plasminogen activator (rt-PA), plasmin, activated protein C, chymotrypsin, factor Xa and trypsin.

The buffer used for al assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_0$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Thrombin (fIIa) Assay

Enzyme activity was determined using the chromogenic substrate, Pefachrome t-PA ($CH_3SO_2$-D-hexahydrotyrosine-glycyl-L-Arginine-p-nitroaniline, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 µL), α-thrombin (50 µl) (the final enzyme concentration is 0.5 nM) and inhibitor (50 µl) (covering a broad concentration range), were combined in appropriate wells and incubated for 30 minutes at room temperature prior to the addition of substrate Pefachrome-t-PA (50 µl) (the final substrate concentration is 250 µM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-nitroaniline), obtained from DiaPharma Group (Franklin, Ohio). All substrates were reconstituted in deionized water prior to use. The final concentration of S-2765 was 250 µM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. *Arch. Biochem. Biophys.* 273:375–388 (1989)]. The enzyme was diluted into HBSA prior to assay in which the final concentration was 0.25 nM.

Recombinant Tissue Plasminogen Activator (rt-PA) Assay rt-PA catalytic activity was determined using the substrate, Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 [L-pyroglutamyl-L-prolyl-L- arginine-p-nitroaniline hydrochloride], which was obtained from DiaPharma group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzloxy-D-lysine-L-prolyl-L-arginine-p-nitroailine dihydrochloride), obtained from Pentapharm Ltd.). The substrate was made up in deionized water followed by dilution in HBSA prior to the assay in which the final concentration was 400 micromolar (about 3-times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroanilide), which was obtained from DiaPharma Group. The substrate was made up in deionized water followed by dilution in HBSA prior to the assay in which the final concentration was 100 micromolar (about 9-times Km). Purified (3×-crystallized; CDI) bovine pancreatic alpha-chymotrypsin was obtained from Worthington Biochemical Corp. The enzyme was reconstituted in deionized water and diluted into HBSA prior to assay in which the final concentration was 0.5 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3×-crystallized; TRL3) bovine pancreatic trypsin was obtained from Worthington Biochemical Corp. The enzyme was reconstituted in deionized water and diluted into HBSA prior to assay in which the final concentration was 0.5 nM.

What is claimed is:

1. A method of treating a condition which is ameliorated by inhibiting or decreasing serine protease activity of matriptase or membrane-type serine protease 1 in a mammal in need of treatment which comprises administering to said mammal a therapeutically effective amount of a compound which inhibits serine protease activity of matriptase or membrane-type serine protease 1 wherein said compound is selected from the group consisting of:

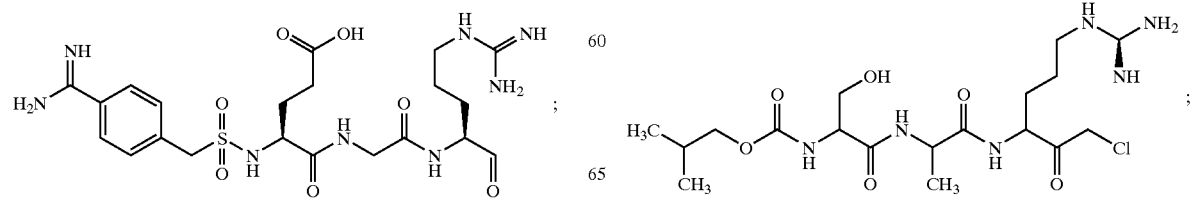

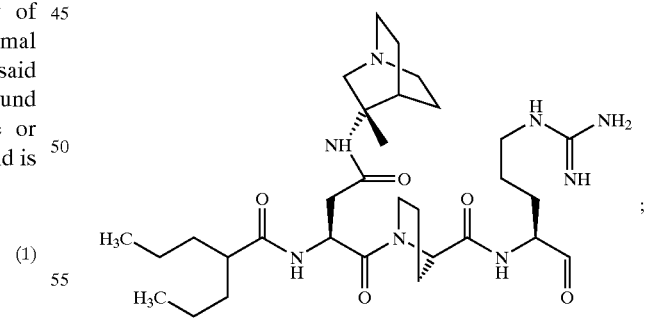

(4)
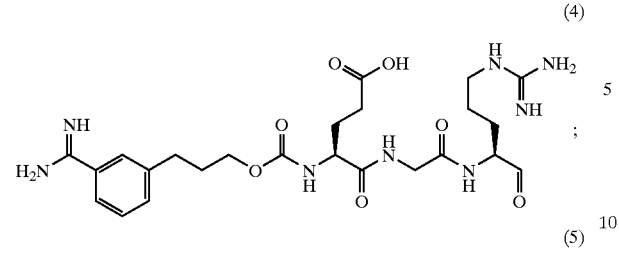
(5)
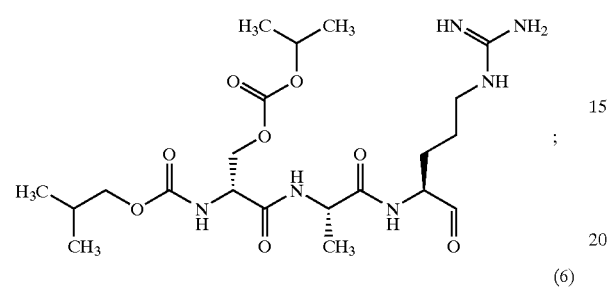
(6)
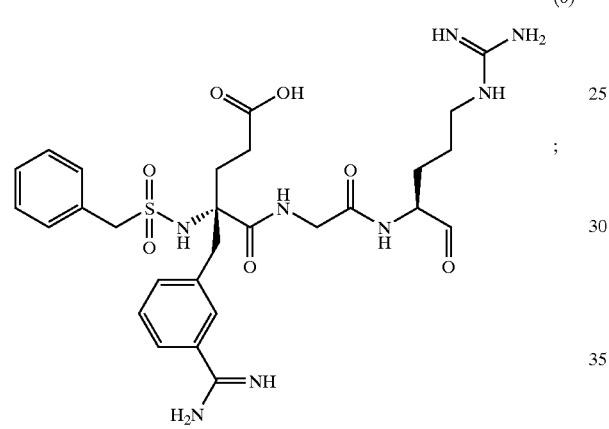
(7)
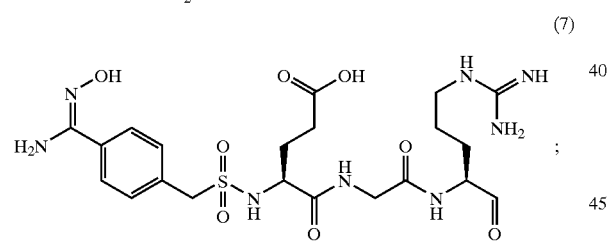
(8)
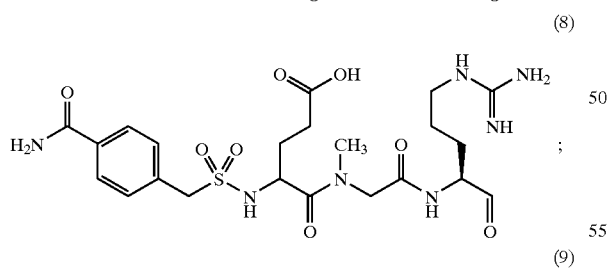
(9)
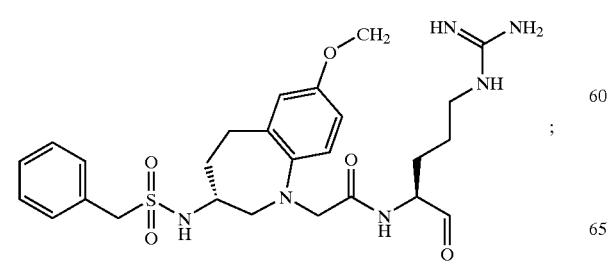
(10)
(11)
(12)
(13)
(14)
(15)
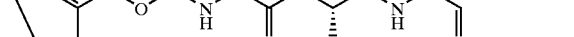

(16)
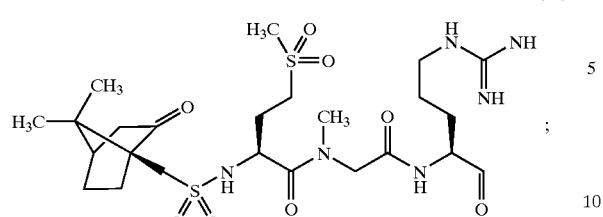
(17)
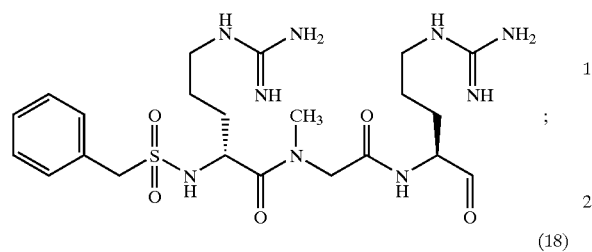
(18)
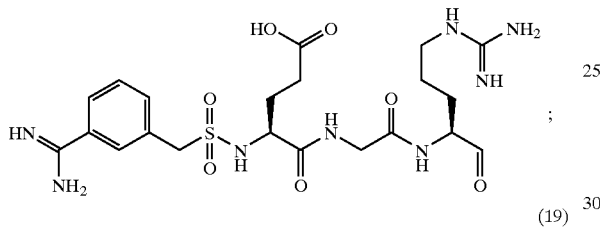
(19)
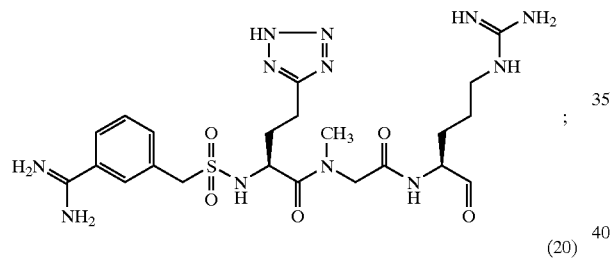
(20)
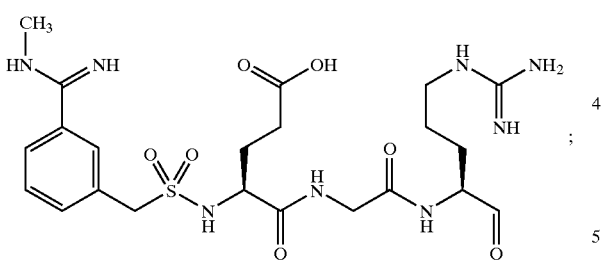
(21)
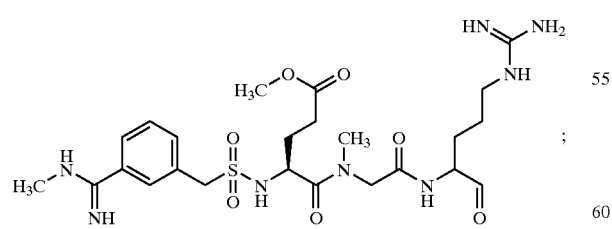
(22)
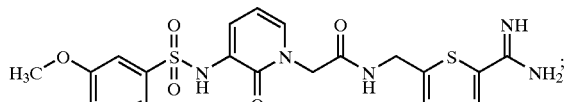
and
(23)
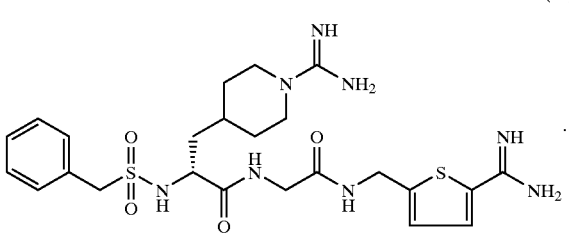
2. A method according to claim 1 wherein said compound has an $IC_{50}$ for inhibition of serine protease activity of matriptase or membrane-type serine protease 1 of 100 nM or less.
3. The Compound of the formula:
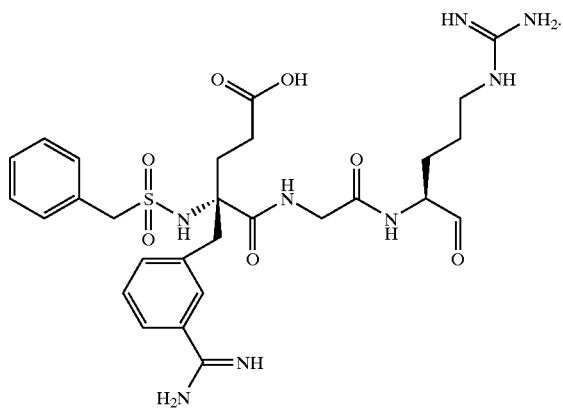
4. The Compound of the formula:
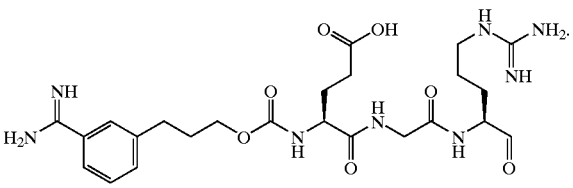
* * * * *